United States Patent
Blake, III

Patent Number: 5,100,376
Date of Patent: Mar. 31, 1992

[54] BODY-CAVITY DRAINAGE AND AUTOTRANSFUSION SYSTEM

[76] Inventor: Joseph W. Blake, III, 88 Main St., New Canaan, Conn. 06840

[21] Appl. No.: 509,306

[22] Filed: Apr. 16, 1990

Related U.S. Application Data

[63] Continuation-in-part of Ser. No. 89,686, Aug. 26, 1987, abandoned.

[51] Int. Cl.$^5$ .............................................. A61M 3/00
[52] U.S. Cl. .......................................... 604/4; 604/320
[58] Field of Search ................ 604/4, 7, 128, 147, 604/251, 262, 320, 355, 319, 406, 410

[56] References Cited

U.S. PATENT DOCUMENTS

| | | | |
|---|---|---|---|
| 3,187,750 | 6/1965 | Tenczar, Jr. ........................ | 604/410 |
| 4,014,329 | 3/1977 | Welch et al. ................... | 604/406 X |
| 4,047,526 | 9/1977 | Reynolds et al. ..................... | 604/4 |
| 4,275,732 | 6/1981 | Gereg ................................ | 604/320 |
| 4,650,477 | 3/1987 | Johnson ............................ | 604/321 |

Primary Examiner—Robert A. Hafer
Assistant Examiner—Kerry Owens
Attorney, Agent, or Firm—Seymour G. Bekelnitzky

[57] ABSTRACT

A disposable, low cost autotransfusion device for suction assisted drainage of fluids from a body cavity of a patient, purification and collection of the desired liquids within said fluids, primarily blood, for reinfusion into said patients said device comprising a) a housing comprising an accumulation chamber, inlet means, in fluid connection with said cavity, through which said fluids enter the chamber, the discharge stem of which terminates in a one-way valve to prevent backflow of gases from said chamber to said cavity in the event the pressure within the cavity becomes less than that within the chamber, filter means to remove unwanted materials, such as debris, from the draining fluids, disposed between said one-way valve and inlet stem and the chamber, first outlet means in fluid connection with a vacuum source through which suction is applied to said chamber and second outlet means in fluid connection with b) an autotransfusion bag comprising outlet means comprising a break seal for connection to the patient for reinfusion of his blood said bag comprising a flexible, collapsible container.

5 Claims, 5 Drawing Sheets

BODY-CAVITY DRAINAGE AND AUTOTRANSFUSION SYSTEM

This is a continuation-in-part of application Ser. No. 07/89,868 filed Aug. 26, 1987, now abandoned.

FIELD OF THE INVENTION

This invention relates to a drainage system for the removal of fluids, e.g., air and blood, from body cavities such as pleural spaces. More particularly it relates to a system for removal and collection of blood from a patient's body cavity for reinfusion of said blood into said patient.

BACKGROUND OF THE INVENTION

Violations of body cavities may occur for any of a number of reasons such as surgery, wounds or, in the case of pleural space invasion, rupture caused by coughing or disease. As a consequence atmospheric air, body gases and other fluids may invade the cavities and, e.g., in the case of pleurae, fill the pleural spaces thereby decreasing the lung capacity. If sufficient fluids accumulate the intimate contact between pleura and lung would be broken thereby preventing the outward pull of the pleura on the lung which results in shrinkage of the lung, i.e., a "collapsed" lung.

Another possible deleterious consequence of such a pleural space invasion would be a mediastinal shift in which the mediastinum, or space between the lungs, which contains such organs as the heart, is displaced from the center thereby compressing said organs. This could result in blood circulation problems and heart cessation.

Thus, it is desirable to remove such invasive fluids from the body cavities as quickly and completely as possible.

Furthermore, blood lost as a result of the above factors must be replaced either by the patient's own blood, i.e., auto-transfusion, or donated blood.

Due to the current atmosphere of fear with respect to AIDS, hepatitis and the like, transfusions of donated blood are becoming more difficult to effect.

Therefore, the demand for autotransfusion of the patient's own blood is growing with a concomitantly increasing need to recover blood lost by the patient due to the factors listed above.

However, to date, the recovery of such blood has been complicated and expensive.

In U.S. Pat. No. 4,540,413 there is described a drainage unit with "blood transfer adapter" which allegedly obviates the above problems. The Patented system depends upon the presence of a liquid seal in the drainage chamber, at the time of connection of the unit to the patient to prevent entry of atmospheric air to the body cavity. Thus, the device must comprise a liquid seal before any drainage of fluids in order to prevent possible pneumothorax before drainage would by sufficient to effect such a seal in the absence of added liquids. Such a system suffers from the major drawbacks of many of the earlier drainage units, that is that an instantaneous decrease of the pressure in the body cavity, e.g., due to gasping respiration of the patient, could result in aspiration of the fluids from the drainage chamber back into the body cavity or the mounting level of fluid in the chamber might impose a progressively increasing resistance to drainage thereby requiring progressively decreased vacuum pressures with its concomitant added monitoring requirements. Furthermore, the advantage of having anti-clotting agents present in the liquid seal (i.e. drainage) chamber would be negated by the fact that as fluid is removed from the drainage chamber some of said agents would also be removed thereby decreasing their concentrations in the drainage sump.

In addition, any debris present in the draining fluid might tend to build up in or around the drainage tube thereby partially or completely clogging it. This might result in slower, or complete cessation of, drainage with the concomitant deleterious effects of poor drainage and/or excess pressure buildup in the body cavity.

Thus, the blood could not "be readily transferred to ... an autotransfusion device" as the blood is not "processed", as indicated therein, but would require additional processing for removal of said debris, etc. as well as the added anti-coagulants. (Emphasis added)

In addition the blood might be foamed as a result of the bubbles passing therethough which would prevent its immediate use for reinfusion. Said bubbling might also cause damage to the blood components.

Other prior art drainage systems are described in my co-pending application Ser. No. 801,205, filed Nov. 25, 1985, which is incorporated herein by reference. The drainage systems, described therein, which obviate the above problems by removing the liquid (water) seal from the drainage chamber to the other, e.g., suction control, chambers suffer from the disadvantage of being cumbersome. Furthermore, their use is position dependent in that any changes in height of the liquid, e.g., as a result of tilting in the suction and/or water seal chambers of, e.g., the Deknatel(TM) Pleur-evac(TM) drainage systems (Deknatel division of Howmedica, Inc., Floral Park, N.Y.) will effect changes in the suction applied to the patient. In addition, changes in water level as a result of evaporation or entrainment in the evacuated gases will also affect accurate control of pressures within the system. To overcome those problems constant monitoring of, or periodic additions of water to maintain the liquid levels of the water seal containing chambers is required with their concomitant potential for operator errors.

The drainage system described in said co-pending application Ser. No. 801,205 avoids those problems by removing all liquid seals and uses purely mechanical means, such as flapper valves on the drainage inlet tube and excess positive or negative pressure relief valves. Therefore, although liquids may be present in the chamber after drainage has been initiated the applied suction cannot be affected by changes in the liquid level therein and the patient is protected from pneomothorax upon attachment to the device. Furthermore, said invention also avoids the cumbersome aspects of the prior art devices by providing a single easily detachable drainage collection chamber to which is removably and sealably affixed a cap comprising all of the controls, valves and inlet and outlet ports from which the collection chamber could be removed without disconnecting the drainage unit from the patient.

The Pleur-evac(TM) ATS, an autotransfusion system based upon the above described Deknatel drainage system, with its concomitant disadvantages, interposes, for autotransfusion purposes, an autotransfusion bag between the patient and the drainage chamber. The autotransfusion bag is flexible but has a rigid top which comprises inlet and outlet stems. Thus, there is always some air present in the bag which contributes to the deterioration of the drained blood exposed thereto and opposes the draining fluids. Furthermore, in order to maintain the autotransfusion bag in an open condition while under vacuum a support frame must be attached to said bag during filling. The bag must then be removed from the frame before being used for reinfusion.

Furthermore, when changing or removal of the bag is required the drainage unit must be disconnected from the patient. This may have undesirable effects if it occurs at an inconvenient time during the drainage process.

Another autotransfusion system, described by Sorensen, comprises a collapsible collection bag which also suffers from the disadvantage of incomplete evacuation due to the top thereof being flat. Furthermore, in order to prevent collapse of the bag, due to the applied suction, which would preclude entry of the drained fluids therein the bag must be placed in another receptacle to which suction is applied and collapse of the bag prevent. Such a system is cumbersome and complex of operation.

The present invention overcomes said disadvantages by providing a compact continuous drainage system which purifies and collects the drainage fluids, prior to the passage thereof into the autotransfusion bag, which does not require a frame to allow filling said bag, and does not require disconnecting of the drainage system from the patient or cessation of suction and/or drainage during the filling and/or removal of the autotransfusion bag.

SUMMARY OF THE INVENTION

Accordingly, it is an object of the present invention to provide an inexpensive, disposable autotransfusion device wherein a body drainage device and autotransfusion liquid collection receptacle comprise a unitary device said device comprising a housing comprising an elongated body comprising an upper wall, a lower wall and a surrounding side wall encompassing a chamber for the accumulation of drained liquids, said chamber having a length greater than that of a height of liquid corresponding to the vacuum to be applied; said elongated body further comprising inlet means in fluid connection with said body cavity, first outlet means in fluid connection with a vacuum source, and second outlet means in fluid connection with a collection bag to receive said liquids for reinfusion to said patient said bag, comprising a flexible material, comprising inlet means for fluid connection to said chamber and further comprising openable outlet means at its other end for fluid connection to the patient.

It is yet another object of the invention to provide a device as described above wherein said receptacle is of the conventional flexible, collapsible type thereby avoiding the need of cumbersome supporting frames.

Another object of the invention is to provide a device as described above further comprising one-way valve means at the discharge end of the inlet means of the elongated body which will close upon the pressure in the body cavity becoming less than that in the chamber thereby preventing backflow of gases from the chamber to the body cavity.

Yet another object of the invention is to provide a device as is described above further comprising filter means spaced from and surrounding said one-way valve to separate said valve from the chamber and remove unwanted solids and liquids from the drained fluids and pass only the purified liquids into the chamber.

Still another object of the invention provides a device as is described above further comprising negative pressure relief and indicating means disposed between said body cavity and said one-way valve.

Another object of the invention is to provide a device as is described above further comprising vacuum pressure control valve to maintain the applied suction at its desired value.

Yet another object of the invention is to provide a device as is described above further comprising hydrophobic filter means disposed between the chamber and said vacuum source to prevent liquids overfilling said chamber from being sucked into said vacuum source and to prevent contaminated air from entering the chamber through the vacuum pressure control valve.

Another object of the invention is to provide a disposable autotransfusion device as described above wherein the lower wall of the elongated body comprises two or more of said second outlet means in fluid connection with at least two collection receptacles in tandem whereby one receptacle may be filled with draining liquids, while a filled one is being removed for reinfusion or disposal, without interruption of the suction connection to the patient.

In accordance with another object of the invention there is provided an autotransfusion device as described above of simplified construction to minimize operation complexity and lower training requirements.

Yet another object of the invention is to provide an autotransfusion device utilizing the wound drainage device, described in my co-pending application Ser. No. 801,205 (filed 11/25/85), as modified by addition of second outlet means for fluid connection to said receptacles.

According to another object of the invention there is provided a disposable autotransfusion device as is described above of unitary construction and low cost to manufacture which is highly compact for shipping and storage.

Another object of the invention is to provide a method of draining fluids from a body cavity of a patient for later reinfusion to said patient comprising the steps of connecting the body cavity to an autotransfusion device comprising a housing comprising an elongated body, lower and upper walls defining an accumulation chamber, said chamber having a length greater than the height of liquid corresponding to the applied vacuum and comprising first outlet means in fluid connection with the vacuum source, second outlet means in fluid connection with a collection bag for reinfusion and inlet means through which said body cavity and said chamber are connected and said bag comprising inlet means in fluid connection with the second outlet means of the elongated body and outlet means for fluid connection to the patient for reinfusion; activating the vacuum source whereby suction is applied to said body cavity causing the fluids therein to enter said chamber until a level is reached therein corresponding to the applied suction at which time the liquid drains into said bag, gravitationally, at a rate approximately that of the drainage of fluids from the body cavity into the chamber until said bag has been filled to the desired extent; sealing of the connector between said housing and collection bag and removal thereof for subsequent use and removal of the drainage unit from the patient for disposal.

The present invention will be better understood and the objects and features, other than those specifically enumerated above, will become apparent when consideration is given to the following details and description, which when taken in conjunction with the annexed drawings, describes, discloses, and illustrates preferred embodiments or modifications of the present invention and what is presently considered and believed to be the best mode of practicing the principles thereof.

Other embodiments or modifications may be suggested to those having the benefit of the teachings herein and are a part of the invention to the extent they fall within the scope and spirit of the subjoined claims.

DESCRIPTION OF THE PREFERRED EMBODIMENTS

Reference is now made to the drawings in which identical parts are designated by the same numbers throughout.

Figure 1:
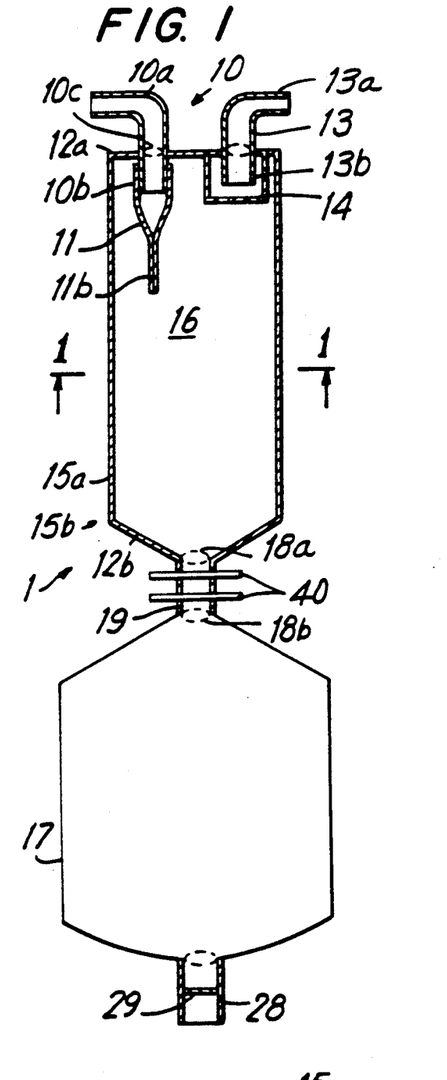
FIG. 1 is a front elevational sectional view of one embodiment of the invention.
Figure 2:
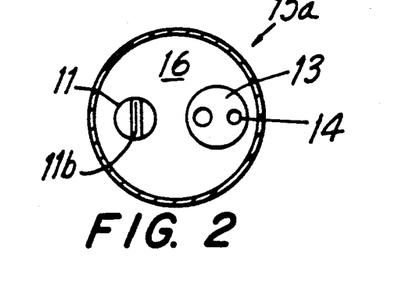
FIG. 2 is a sectional view along line 1—1 of FIG. 1.

FIGS. 1 and 2 illustrate a device, designated by the numeral 1, for the suction assisted drainage of fluids from the body cavity of a patient, and reinfusion of liquids contained therein, such as blood, into said patient. Said device comprises a housing 15b encompassing an accumulation chamber 16. Said housing comprises an elongated body 15a, which may be cylindrical or of any other desired type, comprising an upper wall 12a, a lower wall 12b, inlet means 10, through which fluids drained from said body cavity, by means of a connector (not shown) in fluid connection with said body cavity and said inlet means 10, may pass into said accumulation chamber 16. Said inlet means comprises an intake port 10c from which there extends, upward from the wall 12a of the elongated body an intake stem 10a, and downward from the wall a discharge stem 10b. Said elongated body 15a further comprises outlet means 15a comprising a port from which there extends upward an outlet stem 13a, in fluid connection with a vacuum source (not shown) through connector means (also not shown), and downward an inlet stem 13b. The amount of suction applied to the chamber by the vacuum source is controlled by a regulator valve 14 disposed between said inlet stem 13 and the chamber 16.

The height of said chamber is greater than the length of a column of liquid, contained therein, corresponding to the applied vacuum pressure while its cross-sectional area must be greater than that of the inlet means 10.

Said elongated body further comprises a one-way valve 11, adherent to the discharge stem 10b of the inlet means 10, to prevent flow of gases from said accumulation chamber 16 to the patient if the pressure within the body cavity becomes less than that within the chamber 16. In a preferred modification of the above embodiment of the invention said one-way valve 11 comprises a flapper or duckbill valve the sleeve portion 11b of which is of sufficient length to close over particles contained therein to effect said prevention of backflow of gases.

The chamber 16 is in fluid connection with an autotransfusion collection bag 17 through a connector 19 disposed between the outlet port 18a of the chamber and the inlet port 18b of the bag the cross-sectional areas of said ports and connector being approximately that of the inlet port 10c of the elongated body.

Figure 3:
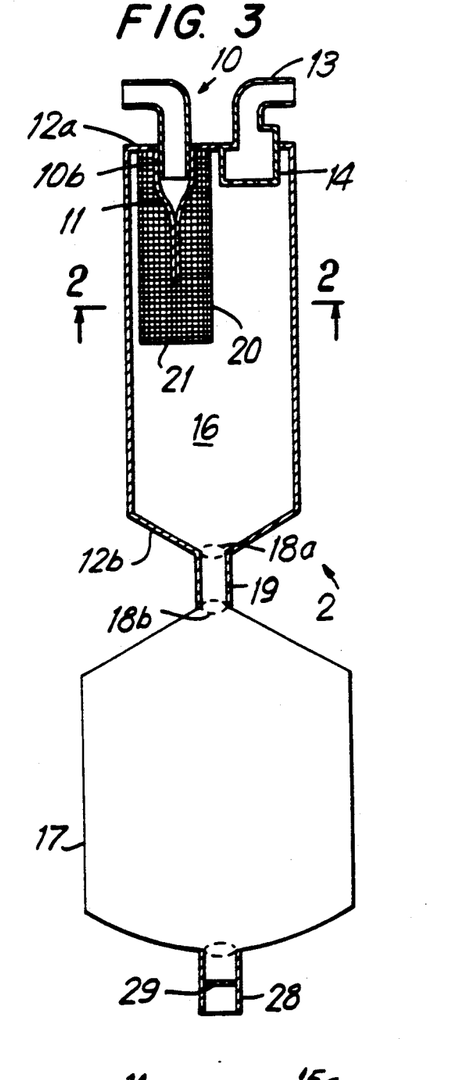
FIG. 3 is a front elevational sectional view of one modification of the embodiment of FIG. 1.
Figure 4:
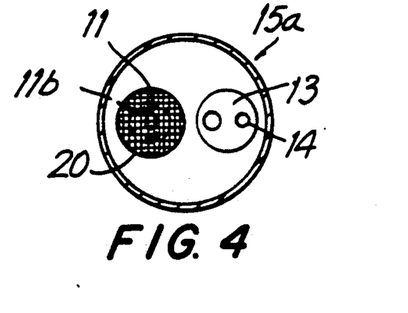
FIG. 4 is a sectional view along line 2—2 of FIG. 3.

Another modification of the above embodiment of the invention, identified by the numeral 2 is illustrated in FIGS. 3 and 4 wherein the discharge stem 10b of the inlet means 10 and the one-way valve 11 are encompassed by filter means 20 comprising a tubular element adherent to said inlet means 10 above its attachment to said one-way valve or spaced from said inlet means and adherent to the wall of the embodiment of the invention whereby the passage of liquids from said one-way valve to said chamber may only be thorugh said filter means and undesired liquids and solids are prevented from entering said chamber 16. The materials of construction, usually a Teflon ® or nylon composition, and pore size of said filter means will be predetermined by the manufacturer in accordance with his requirements. A preferred pore sized is 170 um.

Figure 5:
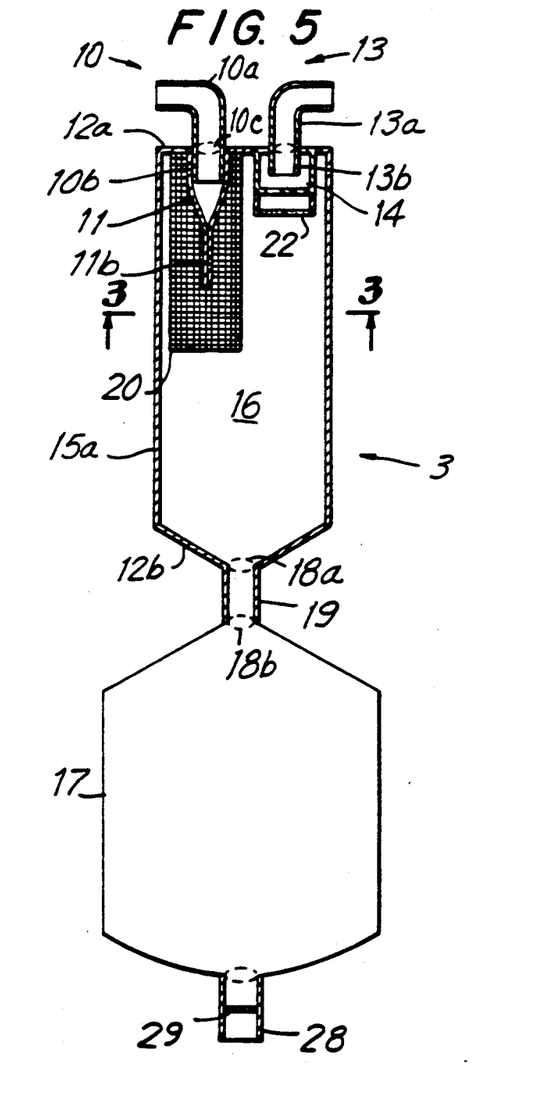
FIG. 5 is a front elevational sectional view of another modification of the embodiment of FIG. 1.
Figure 6:
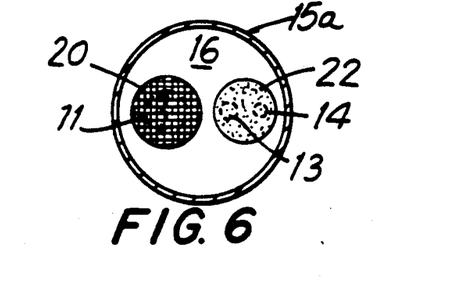
FIG. 6 is a sectional view along line 3—3 of FIG. 5.

Yet another modification of the above embodiment of the invention, as illustrated in FIGS. 5 and 6 provides an autotransfusion device wherein a hydrophobic filter 22 is disposed between said outlet means 13 and the chamber 16 to prevent liquids contained within chamber 16 from being sucked into the vacuum source if said liquid overfills the chamber 16 and rises to the entry end of the outlet means 13. Said filter also prevents contaminants from entering the chamber 16 through vacuum control valve 14.

Figure 7:
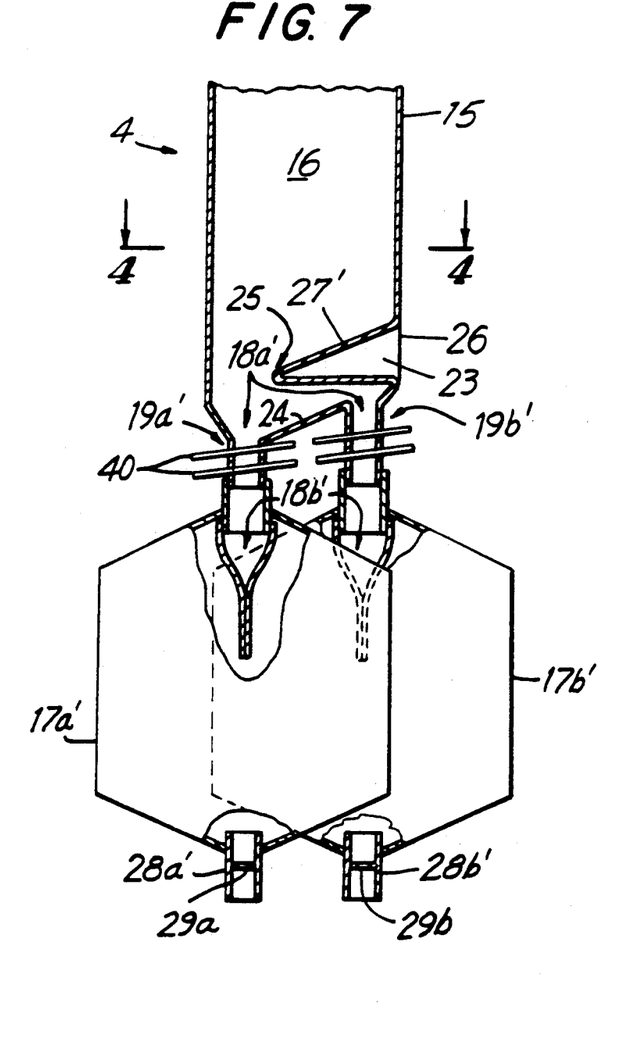
FIG. 7 is a front elevational sectional view of another embodiment of the invention.
Figure 8:
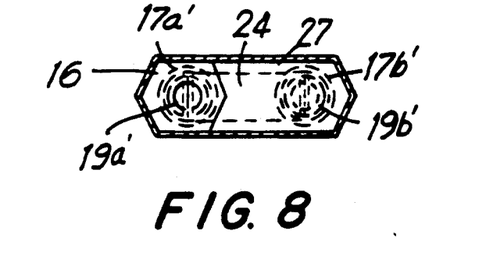
FIG. 8 is a sectional view along line 4—4 of FIG. 7.

FIGS. 7 and 8 illustrate another embodiment of the invention for the succesive filling and removal of two autotransfusion bags without removal of the device from the patient and interrupting the drainage procedure.

In this embodiment of the invention the features of the elongated body are as described above except that the lower wall thereof comprises two outlet ports 18a' in fluid connection with the inlet ports 18b' of two autotransfusion bags 17a' and 17b', through two connectors 19a' and 19b', respectively. Said bags 17a' and 17b', connectors 19a' and outlet ports 18a' and inlet ports 18b' being similar to the bags 17, connectors 19 and outlet ports 18a and inlet ports 18b previously described.

In addition the lower portion of said elongated body comprises a wedge-like lip 23 tapered downward and extending partially to the side, situated between and attached to the front and rear walls of said elongated body with the lowest point thereof positioned over about the center of one of the outlet ports 18a' and the portion 24 of the lower wall 12b between said outlet ports 18a' forms an inclined bridge for fluid connection between said connectors 19a' and 19b'.

Figure 9:
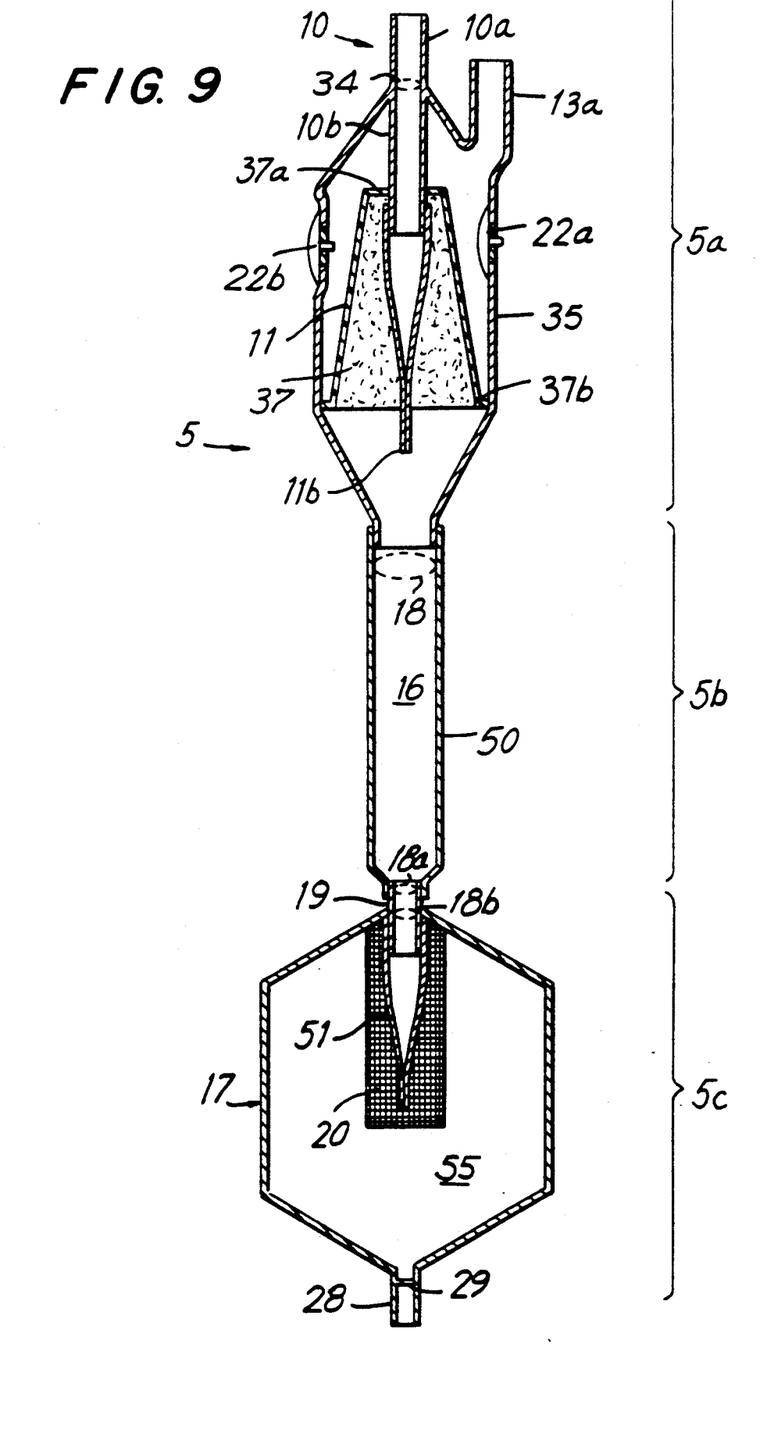
FIG. 9 is an elevational sectional view of another embodiment of the invention.

Yet another embodiment of the instant invention is illustrated in FIG. 9 wherein features common the the above embodiments of the invention are designated similarly.

In this embodiment, designated by the numeral 5, a housing 5a comprises a side wall 35 comprising a first inlet port 34a and first outlet port 34b, a negative pressure control valve 22a and a positive pressure relief valve 22b.

Said housing is in fluid connection, through outlet port 18 with an elongated body 50 which serves as a connector to the autotransfusion bag 17 with which it is in fluid connection through inlet port 18b thereof.

The housing 5a encompasses the discharge end 10b of inlet tube 10, descending from inlet port 10a. Said end 10b is terminated by a one-way valves 11 which will close when the pressure on the inlet side of said valve is less than on the discharge side thus preventing a backflow of gases, usually contaminated, into the body cavity.

The discharge end 10b of the inlet tube and the one-way valves are encompassed by a conical assembly comprising a hydrophobic filter 37, to prevent liquid from entering the suction source inlet if the liquid were to overfill the accumulation chamber and/or prevent contaminated gases from entering the system through the negative pressure control valve 22a, means of attaching same to the upper portion of said discharge end and of separating the portion of the housing thereabove and the negative pressure control 22a and positive pressure relief 22b valves and the first outlet port 34b from the lower portion of the housing whereby suction can only be applied to the body cavity through the hydrophobic filter. Said separation is effected by sealing the upper portion of the hydrophobic filter assembly to the upper portion of the discharge end 10b by seal 37a and at the lower portion of said assembly by a seal 37b between said assembly and the inner wall of the housing. Means of effecting such seals are known in the art and will not be discussed further.

The elongated body 50 encompasses an accumulation chamber 16 from the drained liquids until their passage into the autotransfusion bag 17 through inlet port 18b thereof and, therefore, its cross-sectional area must be greater than that of outlet port 18 of the housing and inlet port 18b of said bag. The height of said connector must be at least as great as a liquid column corresponding to the applied suction.

The discharge end of connector 19 between said elongated body and the autotransfusion bag is terminated by a one-way valves 51 encompassed by a filter 20 for removal of debris, and the like, from the drained liquids.

Thus, the one-way valves and filters 20 may be situated in either the housing or the autotransfusion bag or both.

One-way valves useful in the practice of the invention are known to the art. A preferred type of such valve is the duckbill valve, as illustrated, having a sleeve portion 11b which is long enough to close about a particle of material passing therethrough.

In accordance, with any of the above embodiments of the invention the filter means 20 may be placed at the inlet to the autotransfusion bag instead of the accumulation chamber 16.

The vacuum pressure control valve may be of a fixed or adjustable value type. For purposes of economy a fixed value valve such as an umbrella valve is preferably used.

The elongated body further comprises in its lower wall 12b an outlet port 18a in fluid connection with the inlet port 18b of an autotransfusion bag 17 through connector 19. The autotransfusion bag 17 comprises a hollow collapsible container comprising a flexible material comprising in its upper wall an intake port 18b, in fluid connection with the outlet port 18a, of the elongated body 50a through connector 19. The lower wall of the bag comprises a transfer tube 28 which is closed by means of a break seal 29, or the like. The bag 17 comprises a chamber 55 and is usually shipped and stored in a flattened, evacuated condition whence it is essentially free of contained gases. In use it does not require a frame for support and, therefore, the expense of such a frame and the time consumed in the removal thereof from the bag are eliminated.

Figure 10:
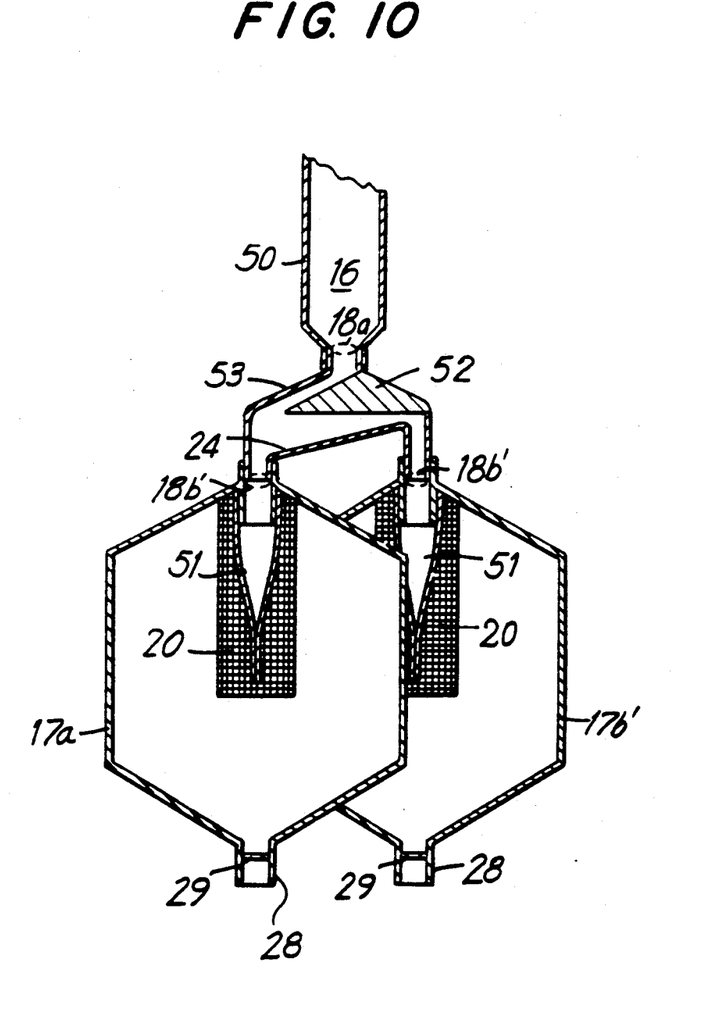
FIG. 10 is an elevational of the lower portion of a modification of the embodiment of FIG. 9.

In a modification of the above embodiment, illustrated in FIG. 10 the elongated body 50 is terminated by a manifold 53 whereby two filled bags of liquid may be obtained for immediated reinfusion without the necessity of disconnecting the drainage and accumulation unit from the patient after the first bag is filled. Said device functions similarly to the embodiment illustrated in FIGS. 7 and 8 in that a wedge-shaped lip 52 directs the drain liquids first into bag 17a' and after said bag has been filled and sealed of, by means described above, from the accumulation chamber 50 said liquids then pass over the portion 24 of the bottom wall which forms an inclined bridge between inlet ports 18b'.

In accordance with another embodiment of the invention there is provided a method of using the autotransfusion devices of the above embodiments.

Thus, in the practice of using the device illustrated in FIGS. 5 and 6 one end of a connector (not shown) is inserted into the body cavity to be drained and the other end thereof is attached to the inlet stem 10a of the device. The outlet end of outlet means 13 is attached to a vacuum source (not shown) through a second connector (not shown). If a fixed value vacuum pressure valve is not used then valve 14 is set at the value desired for the suction. The vacuum source is activated whence the fluids are caused to pass into the device through inlet means 10 and are filtered by filter means 20 whereby only desired liquids, primarily blood are permitted to enter and fill the accumulation chamber 16. This effect will be augmented when the patient inhales creating a positive pressure in the body cavity relative to that on accumulation chamber 16. When the height of liquid in said chamber reaches that corresponding to the applied suction the liquids begin to drain, gravitationally, into the autotransfusion bag 17 which expands to receive said liquds. The rate of filling said bag is approximately that of the drainage from the body cavity maintaining thereby creating a steady state condition whereby the height of liquid within the accumulation chamber 16 is maintained essentially constant.

(In the event the pressure within the body cavity were to drop below that in the accumulation chamber 16 the one-way valve 11 will close preventing backflow of gases from said chamber to the body cavity. The length of the sleeve portion 11b of said one-way valve will be great enough to permit the valve to close sealing off the body cavity of the chamber even if particle(s) of material were to be entrapped within said sleeve portion.)

When a sufficient amount of said has been collected with the bag 17 said bag is sealed off, by two sealing means 40 applied to the connector 19, and severed from the elongated body above between said sealing means. The collected liquids may then be used as required. Normally two sealing means will be used to close the connector and the connector will be severed therebetween. The collected liquids may then be used as desired.

Sealing may be effected by means of clips, pinchcock or screw clamps, and the like.

After collection of liquids has been terminated the connector between the body cavity and device is also sealed, as described above, and the device is removed from the patient and may be discarded or reused.

In a modification of this embodiment of the invention, utilizing the embodiment of the invention illustrated in FIGS. 7 through 9 when the liquid has filled the accumulation chamber 16 to the desired height it is directed, preferentially, by means of the wedge-like lip 23, to container 17a' which fills gravitationally.

After the desired level of filling of said bag has been achieved or if it overflows the liquid then is directed over bridge 24 into bag 17b'.

When it is desired to remove the filled bags from the device two sealing means, as described above, are applied to the connector between the elongated body and the bag to be removed and the connector is severed between said sealing means. Sealing means applied to the connector 19a' whence the liquid is then caused to flow into bag 17b'.

It is also to be understood that, if desired, after the filled bag(s)17 are removed from the device additional bags may be affixed thereto for continued drainage of fluids and collection for later use or disposal.

If desired, the accumulation chambers 16 and bags 17 may further comprise seal-sealing ports for the removal of samples of liquid contained therein or addition of materials such as anti-clotting agents.

With respect to all of the embodiments of the invention the cross-sectional area of the inlet means of the accumulation chamber and the one-way valve must be selected so that, when the one-way valve is opened, the drained fluids may freely flow into the accumulation chamber at a reasonable rate.

In addition, the second outlet means of the embodiment, the inlet means of the collection container and the collector therebetween must be of sufficient cross-sectional area that, when the liquid starts flowing into the container, the liquid will flow therein at a rate approximately equal to the rate at which the liquid enters the accumulation chamber through the inlet means thereof.

The specific values for the above cross-sectional areas will be chosen by the manufacturers of the devices in accordance with the procedure for which a specific embodiment of the device will be used and the liquid flow rate to be expected in that procedure.

There is no maximum height for the accumulation chambers of the inventive devices other than those dictated by practical conditions such as space, handling and the like.

However, there are minimum height requirements which are dictated by the amount of vacuum pressure that would reasonably be expected to be applied to the body cavity.

Thus, liquid will not flow into the autotransfusion bag until the height of the liquid in the accumulation chamber exceeds a value which is proportional to the applied vacuum.

For instance, if the applied vacuum were to be 20 cm. H$_0$O no liquid would flow into the autotransfusion bag until the height of liquid in the accumulation chamber exceeded about 20 cm. As the liquid flows into the autotransfusion bag the liquid level in the accumulation chamber would drop back to 20 cm. at which time liquid would cease to flow into the autotransfusion bag. The liquid would resume flowing into the autotransfusion bag after additional liquid from the body cavity would cause the liquid level in the accumulation chamber to rise above the aforementioned value. This looping process will continue under steady-state conditions whereby the rate of flow of liquid from the body cavity to the accumulation chamber would equal the liquid flow rate from the accumulation chamber to the autotransfusion bag.

This process will continue until drainage into the accumulation chamber will cease or be terminated to permit removal of the filled collection bag. In the latter case the process of draining fluid into the accumulation chamber followed by flow of the liquid therefrom into the collection bag will resume upon attachment of the bag to the outlet means of the accumulation chamber and the connector therebetween and opening of the fluid connection therethrough.

For practical reasons, in view of possible fluctuations in the applied vacuum pressure, the accumulation chamber height must exceed that which is theoretically proportional to the nominal applied vacuum pressure.

In practice vacuum pressures used in drainage procedures are from about 15 to about 50 cm. H$_2$O and the the accumulation chamber height should be from about 20 to about 60 cm. Most drainage procedures use vacuums of from about 20 to about 30 cm. H$_2$O. Therefore, a most preferable range of heights for the accumulation chamber would be from about 25 to about 35 cm.

A consequence of the above is that a device having a specific accumulation chamber height could not be used with a vacuum pressure which is proportional to a height of liquid exceeding the accumulation chamber height. In every drainage procedure it would be necessary to use a model of the device having an accumulation chamber height in the desired range.

Therefore, in practice, it would be necessary to manufacture models of the device having accumulation chamber heights useable with forseeable vacuum pressure ranges. The specific heights chosen would be determined by the manufacturer in accordance with standard procedures.

The embodiments of the invention particularly disclosed and described hereinabove are presented merely as an example of the invention. Other embodiments of the invention, forms and modifications of the invention coming within the proper scope and spirit of the appended claims will, of course, readily suggest themselves to those skilled in the art.

What is claimed is:

1. A method for collecting liquids from a patient, for reinfusion, later use or disposal, by vacuum-effected drainage, at a preset vacuum, of fluids from a body cavity of said patient consisting of the steps of
   A. connecting a vacuum-effected drainage device to the body cavity of said patient by connector means one end of which is in fluid connection with said body cavity and the other end in fluid connection with the entry end of the inlet means of the device wherein said device consists of
      1) a liquid accumulating chamber consisting of a hollow elongated member consisting of an upper wall, a lower wall and side walls wherein the minimum height of the member is at least equal to the maximum height of a column of said liquid, contained therein, which will not flow gravitationally therefrom while said preset vacuum is applied thereto;
- a) chamber inlet means for fluid connection to the patient through which the drained fluids pass from said body cavity to said chamber;
- b) chamber first outlet means for fluid connection of said chamber to a vacuum source;
- and c) chamber second outlet means for fluid connection of said chamber a collection container;

2) a collapsed flexible container, for collection of said liquid, consisting of a closed container having inlet means for fluid connection with said chamber second outlet means for passage of liquid from the chamber to the container;

and 3) connector means to fluidly connect said chamber second outlet means to the inlet means of the container;

B. activating the source, the negative pressure of which has been preset by means of a vacuum pressure control valve, whereby suction is applied to said body cavity, through said accumulation chamber, and the drainage of the body cavity begins and the liquid fills said chamber until its level exceeds said maximum column height whereupon the liquid begins to flow into the container, gravitationally, through said connector means;

C. closing the path between the accumulation chamber and container when the desired amount of liquid has been collected;

D. sealing and removing the filled container;

and E. when the desired extent of drainage using this device has been completed removing same from connection to the patient.

2. The method of claim 1 wherein said container further consists of outlet means to provide fluid connection between said container and the patient for reinfusion.

3. A disposable device for use in vacuum-effected drainage of fluids from a body cavity of a patient, the liquid portion of which fluids are to be disposed of, retained for further use or reinfused into said patient, said device consisting of a housing consisting of
- A. an elongated body consisting of an upper wall, a lower wall and side walls defining an accumulation chamber
  - wherein said lower wall comprises at least two second outlet means for fluid connection to an equal number of collection containers,
  - said side walls comprise a wedge shaped lip tapered from its upper to lower portions, extending to the side, situated between and attached to the front and rear side wall of said elongated body with the lowest point positioned over about the center of one of said second outlet means of said elongated body and
  - the lower wall of said elongated body between said second outlet means providing an inclined bridge for fluid connection thereover between said lower outlet means;
- B. inlet means for fluid connection to the patient through which the drained fluids pass from said body cavity to said chamber;
- C. one-way valve means situated at the discharge end of said inlet means which will close, preventing flow of fluids from said chamber to the patient's body, when the pressure therein decreases relative to that in the chamber;
- D. first outlet means for fluid connection of said chamber to a vacuum source; and
- and E. a vacuum pressure control valve disposed between said vacuum source and the accumulation chamber.

4. The device of claim 3 consisting of a number of collection containers equal to the number of second outlet means on the elongated body.

5. A disposable device for use in vacuum-effected drainage of fluids from a body cavity of a patient, the liquid portion of which fluids are to be disposed of, retained for further use or reinfused into said patient, said device consisting of a housing consisting of
- A. an elongated body consisting of an upper wall, a lower wall and side walls defining an accumulation chamber
  - wherein said lower wall comprises at least two second outlet means for fluid connection to an equal number of collection containers,
  - said side walls comprise a wedge shaped lip tapered from its upper to lower portions, extending to the side, situated between and attached to the front and rear side wall of said elongated body with the lowest point positioned over about the center of one of said second outlet means of said elongated body and
  - the lower wall of said elongated body between said second outlet means providing an inclined bridge for fluid connection thereover between said lower outlet means;
- B. inlet means for fluid connection to the patient through which the drained fluids pass from said body cavity to said chamber;
- C. one-way valve means situated at the discharge end of said inlet means which will close, preventing flow of fluids from said chamber to the patient's body, when the pressure therein decreases relative to that in the chamber;
- D. first outlet means for fluid connection of said chamber to a vacuum source; and
- E. a vacuum pressure control valve disposed between said vacuum source and the accumulation chamber;
- F. a number of collection containers equal to the number of second outlet means on the elongated body; and
- G. connector means attached to the second outlet means of the accumulation chamber and the inlet means of the container to provide fluid connection therebetween.

* * * * *